United States Patent [19]
Bolton

[11] Patent Number: 4,762,491
[45] Date of Patent: Aug. 9, 1988

[54] DENTAL MEASURING INSTRUMENT

[76] Inventor: Wayne A. Bolton, 5302 Scenic Dr., Yakima, Wash. 98908

[21] Appl. No.: 50,903

[22] Filed: May 14, 1987

[51] Int. Cl.$^4$ ............................................. A61C 19/04
[52] U.S. Cl. ........................................ 433/72; 433/3; 33/514
[58] Field of Search .................... 433/72, 3, 68, 69, 73, 433/75; 33/513, 514

[56] References Cited

U.S. PATENT DOCUMENTS

| | | | |
|---|---|---|---|
| 2,465,618 | 3/1949 | Tully | 433/73 |
| 2,787,837 | 4/1957 | Gelfand | 33/513 |
| 3,745,665 | 7/1973 | Shilliday | 33/514 |
| 3,839,801 | 10/1974 | Tappe | 33/514 |
| 3,900,953 | 8/1975 | Posen | 433/72 |

FOREIGN PATENT DOCUMENTS 2716961 10/1978 Fed. Rep. of Germany ........ 433/72

*Primary Examiner*—John J. Wilson
*Attorney, Agent, or Firm*—Roy E. Mattern, Jr.

[57] ABSTRACT

A hand-operated dental measuring instrument used particularly by orthodontists, dentists, and technicians for rapidly indicating and/or monitoring the incisor tooth labial inclination, which is the inclination of the incisor crown to occlusal plane, of a patient's natural teeth or the plaster cast reproductions of a patient's mouth. The procedure can be carried out before, during, and after orthodontic treatment. A dial indicator is fitted with a custom designed indicator arm tip and a dial face, which comprises the active portion of components which are mounted on a rigid injection molded base, which is the passive portion. When the base is brought into contact with the biting surfaces of a patient's natural teeth or reproductions of the teeth, known as dental casts, the indicator arm tip is adjusted to contact the anterior surface of an incisor tooth. By means of right angle geometric principles, the inclination of the incisor crown to the perpendicular is measured and converted from a linear measurement to degrees and is called the incisor labial inclination.

12 Claims, 2 Drawing Sheets

DENTAL MEASURING INSTRUMENT

BACKGROUND

The present invention relates generally to angle measuring or indicating instruments and more particularly to a dental measuring instrument for indicating the labial inclination of central and lateral incisor teeth of both the upper and lower jaw, or maxillary and mandibular jaw, respectively.

The angle formed by a tangent drawn to the anterior or labial surface of the incisor crowns to the perpendicular drawn to occlusal plane is known as labial inclination. Occlusal plane is that plane which connects the incisal or biting edge of a central incisor tooth to the occlusal or biting surfaces of the molar teeth. The measuring of the labial inclinations of the incisor teeth becomes particularly important to the dentist or orthodontist in determining when the esthetic and functional requirements of treatment have been achieved. A ten degree, 10°, difference between the inclination of the maxillary and mandibular central incisors is the goal of treatment, with a range of +5° to +15° for the maxillary central incisor and a range of −5° to +5° for the mandibular central incisor considered acceptable. The ideal goal for labial inclination in the maxillary central incisor is +10°; and 0° for the mandibular central incisor, and orthodontic treatment is directed, at least in part, to the attainment of these angular goals. The establishing of treatment goals for incisor inclination is related also to mathematical tooth size ratios as determined through the use of the Bolton Tooth Size Analysis, 1952.

Previously, the accepted method for determining labial inclination was to draw a tangent to the anterior or labial surfaces of the incisor teeth, whose labial surfaces were traced from a lateral cephalometric head x-ray film. Since superimposing problems exist with the cephalometric headfilm, and since the labial crown surface is not flat, but curved, the possibility of error is great. Also, the procedure requires periodic x-rays and tracings, which is time consuming, expensive, and subjects the patient to additional radiation.

SUMMARY

The present invention provides a convenient, compact measuring instrument which can quickly and easily be brought into contact with either the maxillary or mandibular teeth, and with the adjustment of the indicator arm tip, the labial inclination of the four maxillary and the four mandibular incisors can be measured.

The primary object of this invention is to provide the dentist, orthodontist, or technician with a relatively simple, hand-operated instrument by which the labial inclination can be monitored quickly and easily without subjecting the patient to additional head x-ray films.

In accordance with this invention, I provide an incisor inclination indicating instrument which comprises a hand-held "T" shaped rigid base portion, to which is secured an adjustable dial indicator. The indicator arm tip measures distance in the horizontal plane parallel to the "T" base portion and as it is adjusted to contact the upper or gingival area of the labial surface. Then the dial indicator's hand movement measures the inclination either positively by moving counter-clockwise or negatively by moving in a clockwise direction.

DRAWINGS

In the accompanying drawings of the Dental Measuring Instrument:

DESCRIPTION OF PREFERRED EMBODIMENT

Figure 1:
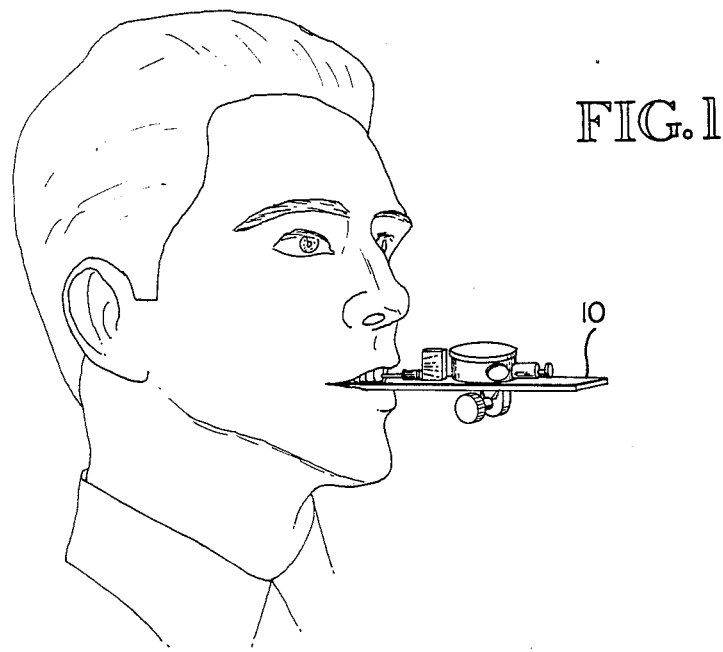
FIG. 1 is a perspective view of the dental measuring instrument positioned in a patient's mouth, to determine incisor inclinations.
Figure 2:
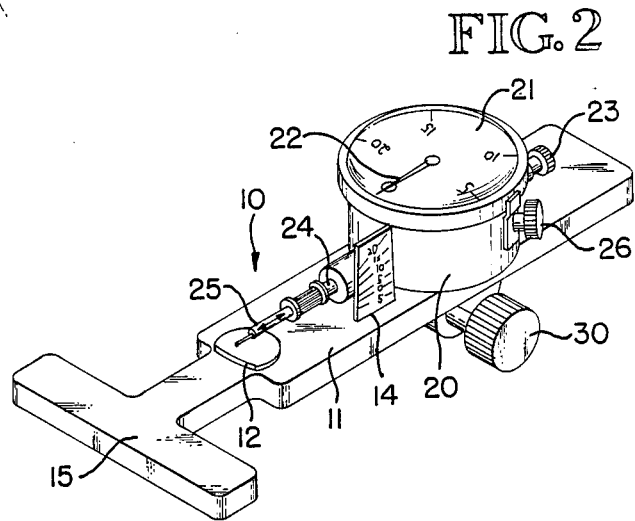
FIG. 2 is a top perspective view of the dental measuring instrument.
Figure 3:
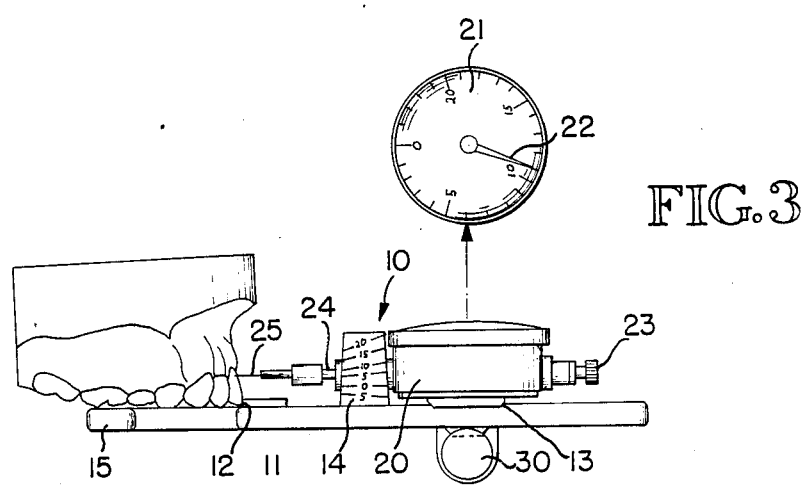
FIG. 3 is a side elevational view of the dental measuring instrument applied to a plaster dental cast of a patient's mouth, with a related top view of the dial indicator face.

As shown in FIGS. 1 and 3 of the drawings, dental measuring instrument 10 is designed to measure in degrees directly, either on the natural dentition or plaster cast reproductions of the patient, the labial inclinations of incisor teeth to occlusal plane. In FIG. 2, the dental measuring instrument 10 itself is shown. It comprises a support 11 with three projections formed of the same plastic material as plate 11 in the injection molding process. Projection 12, 1.5 millimeters in height, forms a single contact stop which contacts the biting or incisal portion of the labial surface of an incisor crown. Projection 13, actually a pair of small projections, act as buttresses for eccentric pin 30. Pin 30 has the round middle portion of its shank formed eccentrically, so when it is rotated either clockwise or counter-clockwise in its opening in the base of the dial indicator 20, it firmly secures dial indicator 20 to the rigid base support 11.

Projection 14, which is 19.0 millimeters in height forms the base for an inscribed protractor scale which registers from −5° to +20°. The oral or occlusal plane segment of support plate 11 designated 15, is in the form of a "T" in order to contact the biting or incisal edge of the incisor being measured and the biting or occlusal surfaces of the molars.

Mounted on support plate 11, is a dial indicator 20, manufactured by MTI Corporation, City of Industry, Calif., which measures in thousandths of an inch, the movement of arm 24. Attached to arm 24 is a custom designed indicator arm tip 25, which is that part which makes actual contact with the labial enamel surface of the incisor tooth crown. The dial indicator face has been customized to read in degrees rather than thousandths, because dental operators are accustomed to working in degrees to describe tooth inclinations and angulations. The linear dimension measured by the movement of indicator arm tip 25, by means of right angle geometric principles, can be converted to degrees of inclination and recorded on dial indicator face 21, through the movement of indicator hand 22. When the indicator hand 22 reads 0°, indicator arm tip 25 and incisal stop 12 form a 90° angle with support base 11.

The indicator arm 24 adjustment screw 23, when rotated in a counter-clockwise direction allows the indicator arm 25 to protrude from the body of the dial indicator 20 to make contact via the indicator arm tip, with the incisor tooth being measured. Indicator face locking screw 26 secures the face portion of the dial indicator, which is adjustable, if minor adjustment needs to be made, in order to begin indicator hand 22 movement from 0°.

In operation the labial inclination measuring instrument is placed in the patient's mouth. In the case of the maxillary teeth the support base 11 is held in contact with the incisor teeth and the molar teeth, and then moved into the mouth until the incisor tooth being measured contacts incisal stop 12. Adjustment screw 23 is rotated counter-clockwise until indicator hand 22 stops its movement, which indicates that indicator arm tip 25 has made contact with the incisor tooth crown. A particular degree marked on the indicator face 21 gives a direct read out in degrees, when the moving hand stops over the particular degree. The indicator arm tip 15 is directed to the center of the tooth crown mesio-distally.

Figure 4:
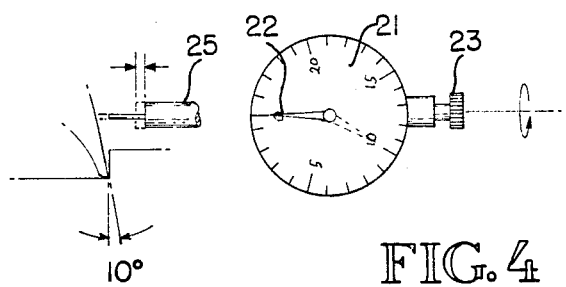
FIG. 4 is a side elevational view of the indicator arm tip in close proximity to an incisor tooth crown, along with a related top view of the dial indicator face, recording a +10° labial inclination indicated by counter-clockwise indicator hand movement.

FIG. 4 demonstrates the action of the dental measuring instrument when a +10° inclination exists.

Figure 5:
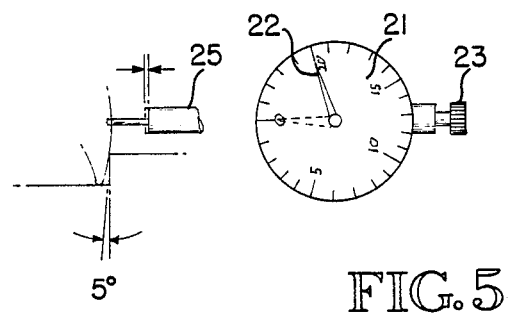
FIG. 5 is a similar view to FIG. 4, demonstrating a −5° labial inclination, indicated by clockwise indicator hand movement.

FIG. 5 demonstrates the action of the dental measuring instrument when a negative −5° inclination angle exists.

Figure 6:
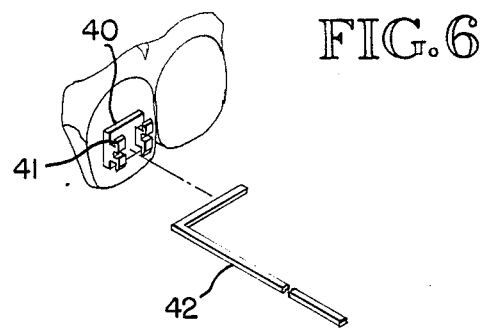
FIG. 6 is a perspective view of a typical orthodontic appliance bracket bonded to a maxillary central incisor tooth, receiving a close tolerance rectangular wire into its rectangular slot, for use, as shown in FIG. 7.
Figure 7:
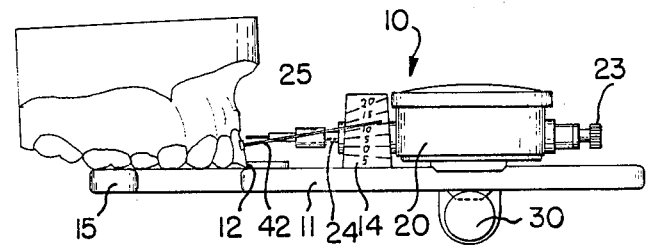
FIG. 7 is a side view demonstrating an alternate method of determining labial inclination, if an anatomical tooth crown defect or orthodontic bracket interference exists, whereby the extending rectangular wire shown in FIG. 6 is used.

FIG. 6 demonstrates the action to be taken in those rare instances when an anatomical defect in the incisor crown exists, or orthodontic appliance bracket placement is such that the bracket interferes with the indicator arm tip 25 making contact with the tooth enamel surface. Therefore, a close tolerance rectangular wire 42 is fitted to a rectangular slot 41 of the orthodontic bracket 40 and projects forward, or anteriorly, to contact the protractor scale 14, as shown in FIG. 7, and records the inclination angle of the bracket slot 41, which is the same as recording the incisor crown inclination since the bracket slot forms a 90° angle with the incisor crown.

This dental measuring instrument 10 is used in conjunction with an orthodontic analysis system called Tooth Size Labial Inclination Analysis or "Torque Analysis", of which the original Bolton Tooth Size Analysis is an integral part. It is used conveniently and effectively as a dental measuring instrument to enable the dental operator to quickly determine the labial inclination of incisor teeth with much greater accuracy, plus eliminating the need for expensive, time consuming X-rays of the head with their accompanying radiation risks.

While a single preferred embodiment of the invention has been illustrated and described in detail, it should be understood that various modifications as to details of construction and design may be resorted to without departing from the spirit of the invention or the scope of the following claims.

I claim:

1. A dental measuring instrument used by dentists and orthodontists to determine the labial inclination of maxillary and mandibular incisor teeth, and the measurements obtained are incorporated into the Bolton tooth size labial inclination analysis, comprises:

(a) an elongated base, which is "T" shaped, whereby a cross portion of the "T" base is insertable in a patient's mouth to be held in contact with the patient's teeth, and the stem portion of the "T" base has a positioning projection to be contacted by the patient's incisor tooth, thereby limiting any farther insertion of the "T" shaped base into the patient's mouth;

(b) a dial indicator mounted on the elongated base to determine a linear dimension, which is made in a plane parallel to the plane established by the elongated base, and this dial indicator has a rotating pointing hand and dial face indicia;

(c) a dial indicator adjustment screw of the dial indicator is turned to move an indicator arm;

(d) an indicator arm of dial indicator, when moved by the dial adjustment screw, protrudes to contact the mesio-distal center of the incisor crown of a patient's incisor tooth; and the linear dimension is converted by the dial indicator, whereby a rotating pointing hand simultaneously moves over dial face indicia of the dial indicator to reach an angle of inclination of the patient's incisor tooth.

2. A dental measuring instrument, as claimed in claim 1, whereby, when the indicator arm terminates over the positioning projection in a plane perpendicular to the elongated "T" shaped base, the rotating pointing arm is over a zero reading of the dial face indicia.

3. A dental measuring instrument as claimed in claim 2, wherein the indicator arm has a tip of smaller dimensions serving to contact the incisor teeth.

4. A dental measuring instrument, as claimed in claim 2, comprising, in addition; an upstanding vertical planar projection, integral with the elongated "T" shaped base, and indicia on this projection presenting angles of inclination, whereby, when an extending wire is positioned in a rectangular slot of an orthodontic bracket on a patient's incisor tooth, this extending wire extends to the planar projection and over the indicia thereof presenting an observer with an angle of labial inclination.

5. A dental measuring instrument, as claimed in claim 2, wherein the elongated "T" shaped base has a receiving opening, two depending bottom spaced abutments, and a cooperating cross pin, having an eccentric circular abutment, to receive and then to secure in place the dial indicator as the cooperating cross pin is rotated until tight.

6. A dental measuring instrument as claimed in claim 2, comprising, in addition, an indicator face locking screw, whereby the dial face indicia of the dial indicator, is rotated through a small arc as may be necessary to establish a zero reading.

7. A dental measuring instrument for determining the labial inclination of maxillary and mandibular incisor teeth and incorporating the data received into the Bolton Tooth Size Labial Inclination Analysis, comprises:

(a) an elongated base, commencing as a narrower finger held portion and terminating as a wider portion to create at least three planar locations, to first receive centrally the contact of an incisor tooth, and then the respective contacts of a left posterior tooth, and a right posterior tooth, and having a positioning means to locate the incisor tooth.

(b) a dial indicator mounted on this elongated base, on the narrower finger held portion thereof, such that the linear dimension which it measures is parallel to the plane established by the elongated base, and this dial indicator has a rotating pointing arm, and dial face indicia;

(c) movable indicator arm of the dial indicator;

(d) dial indicator adjustment screw of the dial indicator allows the movement of the indicator arm to contact the mesio-distal center of the incisor tooth crown, thus measuring the amount of its labial inclination in degrees; because by utilizing mathematical principles, i.e. right angle geometry, the linear dimension measured in thousandths of an inch is converted to degrees and recorded on a custom designed indicator face of the dial indicator.

8. A dental measuring instrument, as claimed in claim 7, whereby, when the movable indicator arm terminates over the positioning means on the one piece elongated base, the rotating pointing arm of the dial indicator is over a zero reading of the dial face indicia.

9. A dental measuring instrument as claimed in claim 8, wherein the indicator arm has a tip of smaller dimensions serving to contact the incisor teeth.

10. A dental measuring instrument, as claimed in claim 8, comprising, in addition; an upstanding vertical planar projection, integral with the elongated base, and indicia on this projection presenting angles of inclination, whereby, when an extending wire is positioned in a rectangular slot of an orthodontic bracket on a patient's incisor tooth, this extending wire extends to the planar projection and over the indicia thereof presenting an observer with an angle of labial inclination.

11. A dental measuring instrument, as claimed in claim 8, wherein the elongated base has a receiving opening, two depending bottom spaced abutments, and a cooperating cross pin, having an eccentric circular abutment, to receive and then to secure in place the dial indicator as the cooperating cross pin is rotated until tight.

12. A dental measuring instrument as claimed in claim 8 comprising, in addition, an indicator face locking screw, whereby the dial face indicia of the dial indicator, is rotated through a small arc as may be necessary to establish a zero reading.

* * * * *